United States Patent [19]
Barnes

[11] Patent Number: 5,891,079
[45] Date of Patent: Apr. 6, 1999

[54] METHOD FOR PROVIDING STABILITY TO THE ELBOW JOINT

[75] Inventor: William M. Barnes, Cheyenne, Wyo.

[73] Assignee: Brown Medical Industries, Spirit Lake, Iowa

[21] Appl. No.: 17,304

[22] Filed: Feb. 2, 1998

[51] Int. Cl.⁶ ................................................. A61F 13/00
[52] U.S. Cl. .............................. 602/61; 602/20; 602/62; 128/881
[58] Field of Search ................... 602/20, 23, 60, 602/61, 62, 26; 473/212, 458, 450, 464, 473, 106; 273/DIG. 30; 128/881

[56] References Cited

U.S. PATENT DOCUMENTS

| | | | |
|---|---|---|---|
| 3,785,371 | 1/1974 | Lewis | 602/20 |
| 3,934,583 | 1/1976 | Hollingshead et al. | 602/62 |
| 5,624,388 | 4/1997 | Lehr | 602/20 |
| 5,785,673 | 7/1998 | Billotti | 602/13 X |

*Primary Examiner*—Richard J. Apley
*Assistant Examiner*—Kim M. Lee
*Attorney, Agent, or Firm*—Zarley, McKee, Thomte, Voorhees & Sease

[57] ABSTRACT

An elbow brace of the present invention is adapted to provide stability to the elbow joint. The elbow brace is comprised of an elastic sleeve and an elastic strap. After the sleeve is placed over the arm of a person, the elastic strap is attached to the sleeve by Velcro fasteners and wrapped in a figure eight configuration. The elastic strap is secured to the sleeve in different ways depending on the part of the elbow joint that needs to be supported. The elbow brace of the present invention can be used either to alleviate pain of an existing injury or as a preventative device to prevent injury. The brace can be used to modify various biomechanical actions that take place in the arm including extension or hyper-extension of the elbow, hyper-pronation of the hand, and/or hyper-supination of the hand.

14 Claims, 3 Drawing Sheets

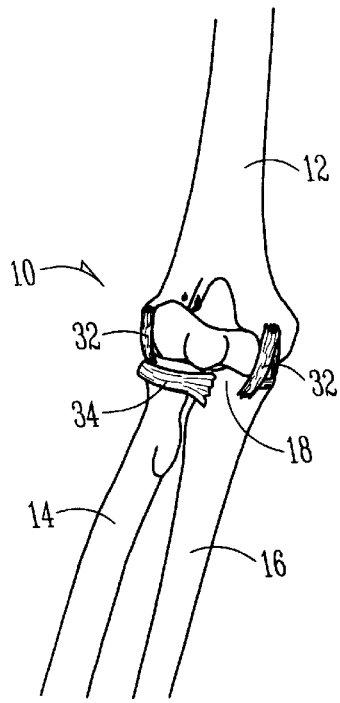
Fig. 1
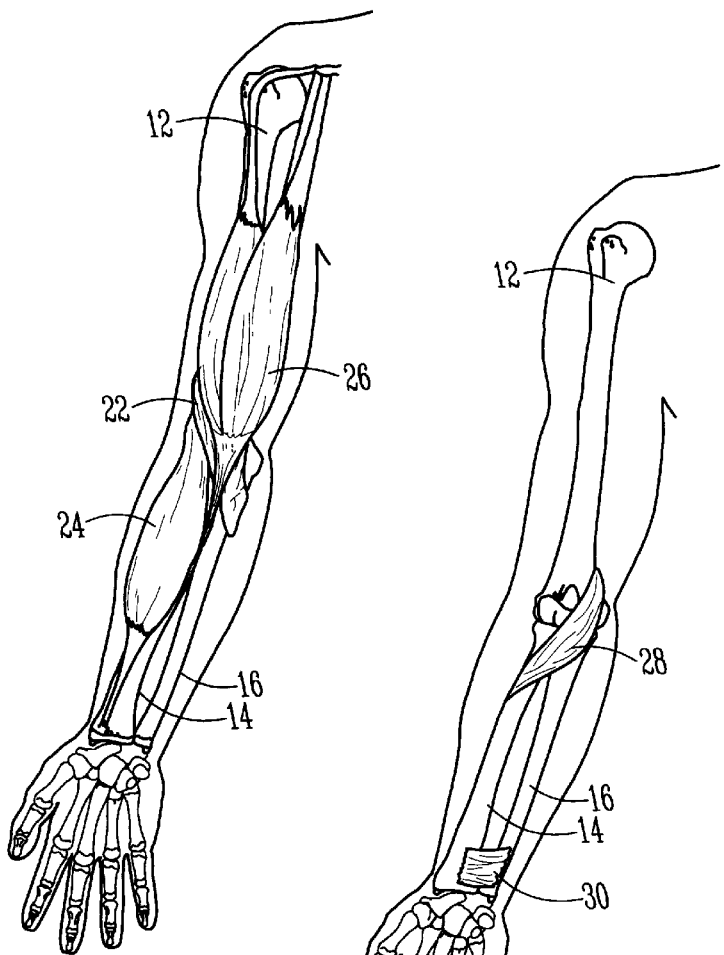
Fig. 2
Fig. 3
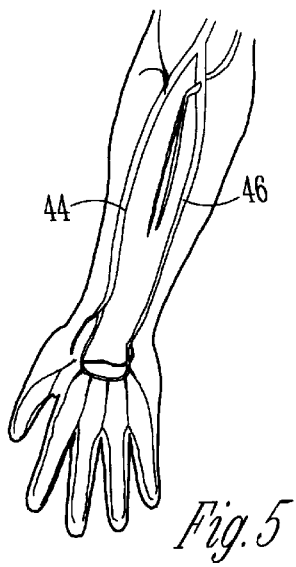
Fig. 5
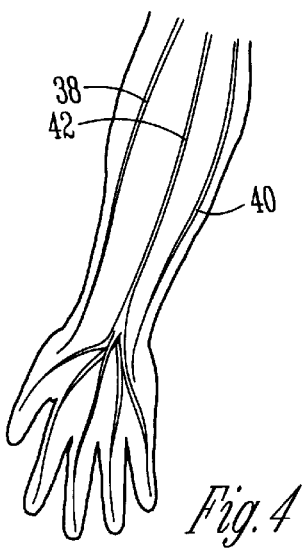
Fig. 4

METHOD FOR PROVIDING STABILITY TO THE ELBOW JOINT

BACKGROUND OF THE INVENTION

1. Field of the Invention

The present invention relates to the elbow joint. More particularly, though not exclusively, the present invention relates to an apparatus and method for providing stability to the elbow joint to prevent extension and/or hyper-extension of the elbow, hyper-pronation of the wrist, and hyper-supination of the wrist.

2. Problems in the Art

There are three main biomechanical actions that take place in the arm which result in various problems. The impacting actions are extension of the elbow, pronation of the wrist (the act of turning the hand so the palm faces downward), and supination of the wrist (the act of turning the hand so the palm faces upward). Each of these actions are standard motions for various physical activities.

Various sports that have elbow injuries include any throwing sport, any racquet sport, and rodeo riders. In addition, various occupations that have elbow injuries include carpet laying, sewing, and meat packing, for example. The frequent names of the elbow injuries are "Tennis Elbow", "Little League Arm", etc.

To understand the cause of these injuries it is important to understand the anatomical structure of the elbow. FIGS. 1–5 show various anatomical views of an arm 10. The anatomical structure of the elbow begins with the bones of the elbow. There are three bones in the elbow joint including the humerus 12, the radius 14, and the ulna 16 (FIG. 1). The primary protection for an elbow joint, so as to prevent hyper-extension, is the olecranon process, which is the superior end 18 of the ulna 16, and rests between the medial and lateral epicondyles of the humerus 12. Upon full extension, the olecranon acts as a "door stop". The radius 14 is considered a free-floating bone in the forearm. Its positioning and guidance for function is controlled by a ligament attachment between the radius 14 and ulna 16, the interosseous ligament (not shown), and muscles that connect the upper arm to the forearm and the radius 14 and ulna 16. These muscles are the Brachialis 22, the Brachioradialis 24, the Supinator (not shown), the Biceps brachii 26, the Triceps brachii (not shown), the Pronator teres 28, and the Pronator quadratus 30 (FIGS. 2 and 3). The superior end 18 of the ulna 16 is attached to the lateral and medial condyles of the humerus 12 by the lateral and medial collateral ligaments 32. The annular ligament 34 attaches the radial head and the superior end 18 of the ulna 16 (FIG. 1).

FIGS. 4 and 5 illustrate the nerves and arteries, respectively, supplying the elbow joint, wrist, and hand. FIG. 4 illustrates the Radial nerve 38, the Ulnar nerve 40, and the Median nerve 42. FIG. 5 illustrates the Radial artery 44 and the Ulnar artery 46. These nerves and arteries are most directly effected by swelling of the tissue of the tendons and muscles that apply pressure on the nerves and arteries.

When the elbow is in a fully extended position, combined with the hyper-pronation of the wrist, damage can occur in the Brachioradialis 24 in the superior third of the muscle. This damage is usually in the form of muscle fiber tear, commonly referred to as "strain". When this injury heals, scar tissue develops. The amount of scar tissue that develops is reflective in the amount of pressure that is present over the radial nerve 38 (FIG. 4). Pressure to the radial nerve 38 can be as insignificant as soreness of the muscle, or can be more serious resulting in numbness and the inability for proper muscle function.

There have been various attempts in the prior art to address the problems discussed above. As discussed above, many people experience elbow difficulties during participation in rodeos, throwing, and racquet activities. All of these activities create a strong possibility for the elbow to be hyper-extended. In each of these activities, variations of the motions of the arm occur which involve other actions, such as the hyper-supination and hyper-pronation of the wrist.

One prior art device is known as a "Tennis Elbow" brace. The "Tennis Elbow" brace is a counterforce brace whose mechanical function is to displace the origin of the muscles and tendons attaching to the condyles of the humerus 12. The danger of this type of prior art base is that the shortened muscles and tendons are forced to perform their normal functions usually accomplished by a longer structure. This is due to the fact that the "Tennis Elbow" brace is simply an elastic strap attached with Velcro on the forearm below the elbow. The primary motivation in the treatment of tennis elbow is the relief of pain. The brace described above attempts to allow an injured tendon or muscle to have a new "fictitious" origin. The dangerous situation this creates is that the tendon or muscle is normally of a natural length, is now expected to perform the same function with less fiber as that amount determined by the placement of the strap.

Other prior art devices also have shortcomings. Some prior art devices simply provide warmth for the injured area, comfort to the user, or tension straps to provide a sense of stability. Other devices have the primary purpose of reinforcing the medial and lateral collateral ligaments. All of these types of prior art devices are used by individuals post-traumatic, as opposed to being used to prevent injuries.

FEATURES OF THE INVENTION

A general feature of the present invention is the provision of a method and apparatus for providing stability to the elbow joint which overcomes problems found in the prior art.

A further feature of the present invention is the provision of a method and apparatus for providing stability to the elbow joint using a sleeve applied to an elbow and a separate elastic strap secured to the sleeve in a figure eight configuration.

Further features, objects and advantages of the present invention include:

A method and apparatus for providing stability to the elbow joint which helps to prevent injuries.

A method and apparatus for providing stability to the elbow joint which helps prevent the elbow from getting into a hyper-extended position.

A method and apparatus for providing stability to the elbow joint which can be used to prevent injury or prevent aggravation of a preexisting condition.

A method and apparatus for providing stability to the elbow joint which improves the amount of control individuals have on their movements.

A method and apparatus for providing stability to the elbow joint in which the user has the option of treating elbow hyper-extension and hyper-supination, and/or elbow hyper-extension and hand hyper-pronation.

A method and apparatus for providing stability to the elbow joint which anatomically and correctly provides stability through a strapping method.

These as well as other features, objects and advantages of the present invention will become apparent from the following specification and claims.

SUMMARY OF THE INVENTION

The elbow brace of the present invention is used to provide stability to the elbow joint. The invention is comprised of an elastic sleeve adapted to fit over the arm of a user and an elastic strap. The brace is applied by applying the elastic sleeve to the arm, securing one end of the elastic strap to a first side of the sleeve, wrapping the strap around the posterior portion of the sleeve to the opposite side of the sleeve in a figure eight configuration, and securing the opposite end of the strap to the sleeve. The elbow brace supports and protects certain parts of the elbow depending on method used to wrap the strap.

BRIEF DESCRIPTION OF THE DRAWINGS

FIG. 1 is an anterior view of a right arm showing the bones and ligaments of the elbow.

FIG. 2 is an anterior view of a right arm showing the muscles of the arm.

FIG. 3 is an anterior view of a right arm showing the forearm pronators.

FIG. 4 shows a right arm illustrating the nerves supplying the elbow joint, wrist, and hand.

FIG. 5 shows a right arm illustrating the arteries supplying the elbow joint, wrist, and hand.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalencies which may be included within the spirit and scope of the invention.

As discussed above, the impacting actions of the arm include (1) extension and/or hyper-extension of the elbow, (2) hyper-pronation of the wrist, and (3) hyper-supination of the wrist. These three main biomechanical actions that take place in the arm can be modified by the use of the brace of the present invention.

Figure 6:
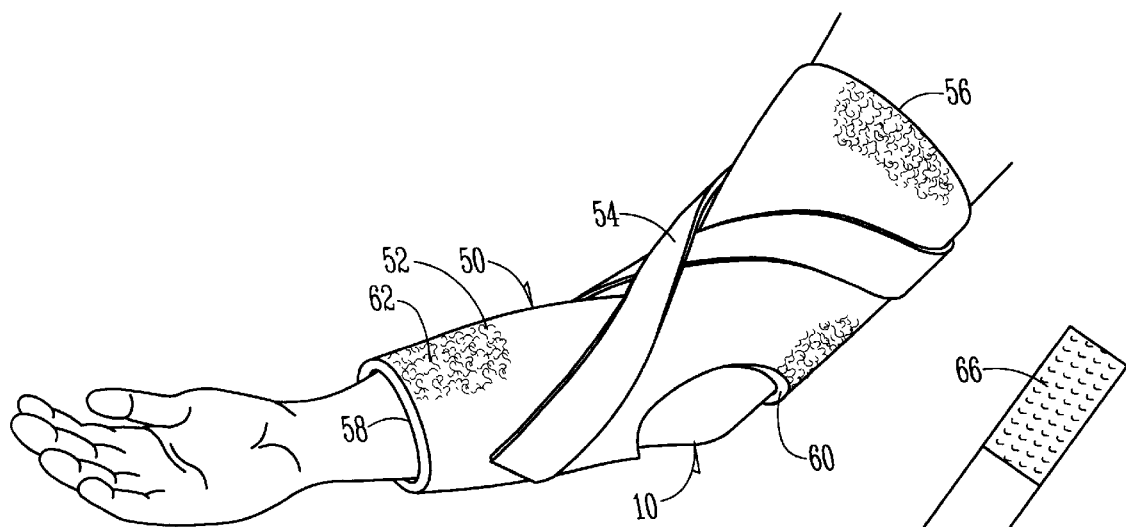
FIG. 6 shows the brace of the present invention in use.

FIG. 6 shows a brace 50 applied to the arm 10 of a person. The brace 50 is comprised of a sleeve 52 and a strap 54. The sleeve 52 is preferably comprised of a neoprene elastic material having an upper opening 56 and a lower opening 58. The upper opening 56 is larger than the lower opening 58 and is adapted to fit around the upper arm of the person. The lower opening 58 is adapted to fit around the forearm. The sleeve 52 includes a posterior opening 60 which, as shown, is positioned around the elbow of the arm 10. The outer surface of the sleeve 52 is comprised of a "loop" fastener 62, for example a Velcro fastener, and is adapted to attach to a mating hook fastener. Preferably, the entire surface of the sleeve 52 is covered by the loop fastener 62. Alternatively, selected portions of the sleeve 52 could be attached to a piece of "loop" fastener. In this case, a first location where the loop fasteners would be attached include a position posteriorly of the forearm section of the sleeve, attached at a midpoint of the ulna between the wrist and the elbow. A second position includes the posterior section of the sleeve at a point midway between the olecranon process and the superior end of the humerus the alternative sleeve configuration is not shown.

Figure 7:
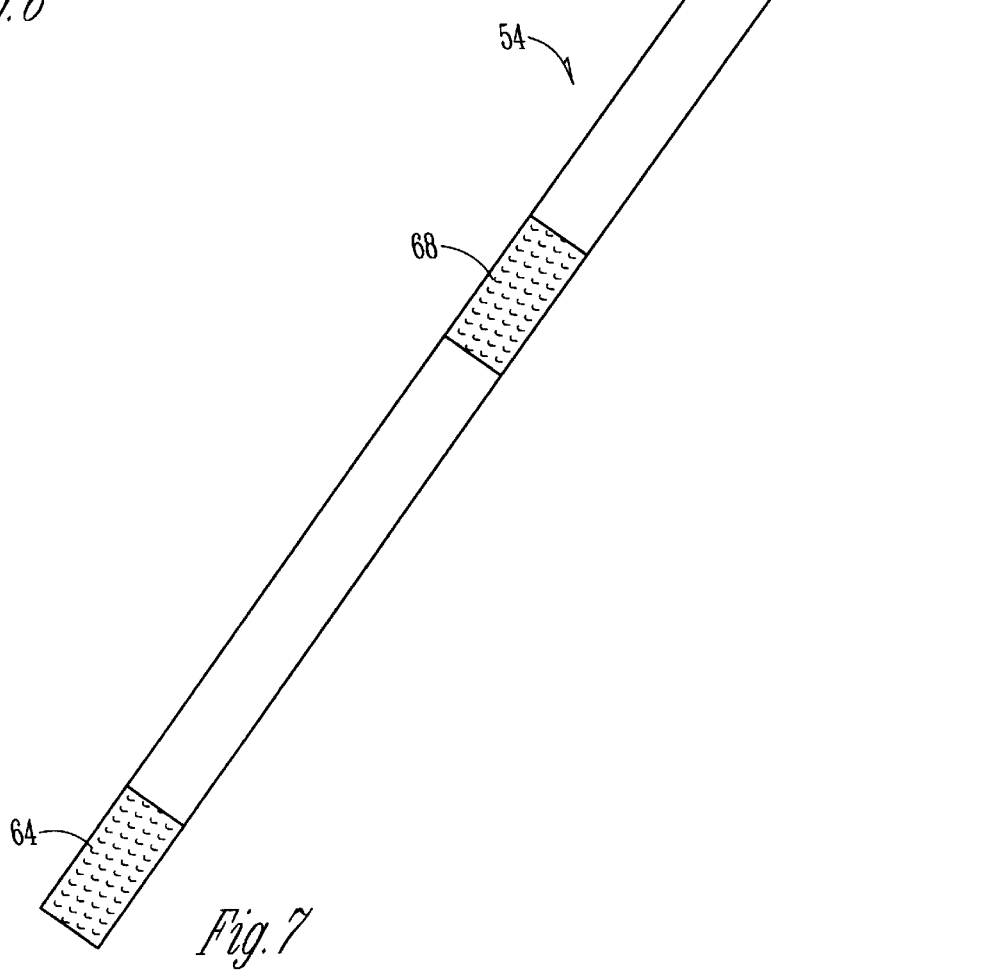
FIG. 7 is a view of the strap used with the present invention.

FIG. 7 illustrates the elastic strap 54 in a flattened position. Preferably, the strap is comprised of a 1½ inch wide elastic strap with "hook" fasteners on the same side of the strap at each end and at the center. As shown in FIG. 7, first, second and third fasteners 64, 66 and 68, respectively are positioned at the two ends and at the center of the strap 54.

The application of the brace 50 is instrumental in limiting and/or preventing an initial injury, or limiting an aggravation of a preexisting condition. The brace 50 accomplishes this by the method in which the strap 54 is applied (described in detail below). With the arm 10 in the position where the hand is in a supinated position and the end of the strap 54 ending on the anterior/lateral area of the forearm, the Pronator teres, the Pronator quadratis, and the annular ligament can be assisted and/or protected. When the strap 54 is ending on the anterior/medial area of the forearm, the same structures are affected along with the medial collateral ligament. When the strap is applied in either manner, as described below, the brace 50 has the capability to eliminate, or assist in reducing the degree of hyper-extension occurring in the elbow. By limiting the elbow from getting into the hyper-extended position, the pressure on the radial nerve 38 and/or the incorporation of a weakened muscle due to injury, can be achieved.

The figures illustrate two methods of applying the brace 50 depending on which part of the elbow is hurting or needs to be protected. Following are descriptions on the two alternate methods. With both methods, the sleeve 52 is first positioned around the arm 10 as illustrated in the Figures. The sleeve 52 is put on the arm with the opening 60 on the posterior side of the elbow. The olcranon process is centered in this opening. The strap is then applied depending on the desired method.

The manner in which the strap 54 is applied compensates for different ligaments and tendons within the elbow structures that are most prone to some type of injury due to extension of the arm via throwing, holding, lifting, etc. (motions where the arm is extended). The following methods link the elbow anatomy of the elbow with the structure of the brace 50 in a unique way.

Figure 9:
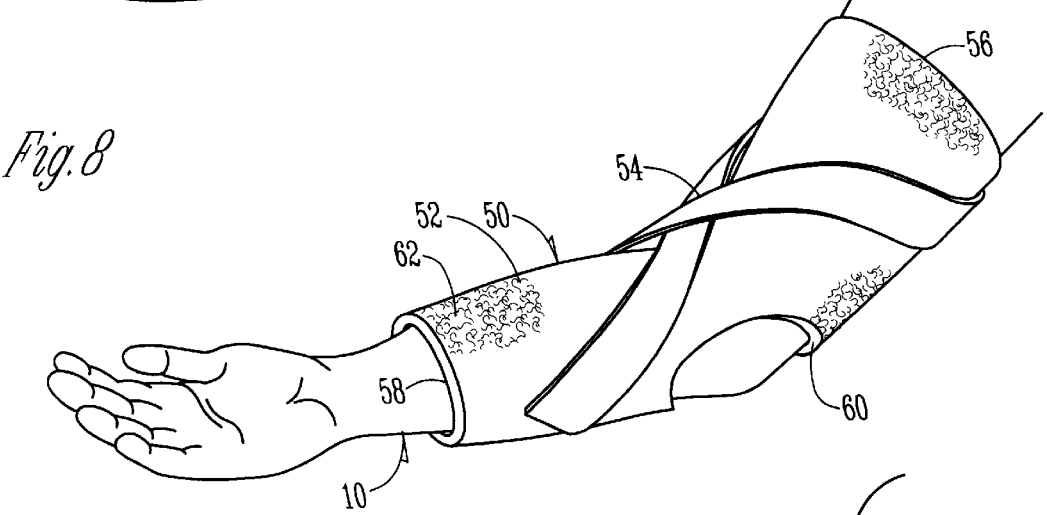
FIG. 9 shows the brace of the present invention applied in an alternate manner.
Figure 10:
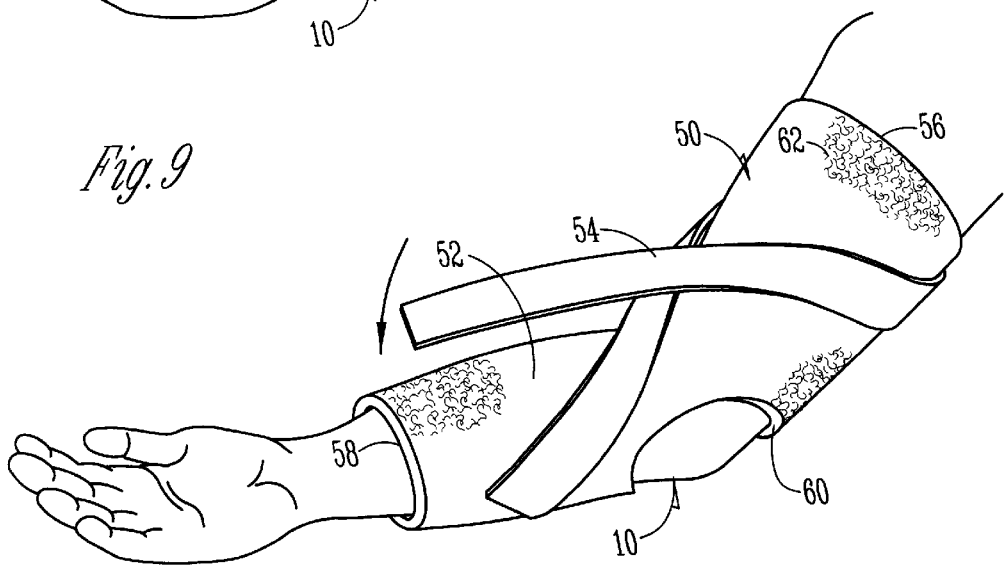
FIG. 10 illustrates the application of the brace shown in FIG. 9.

The first method of applying the strap 54 is used to assist in preventing and treating both elbow hyper-extension and hand hyper-pronation. FIGS. 9 and 10 illustrate the brace 50 applied to the right arm of the wearer using this method. The steps include:

1. The elbow is flexed 90° with the hand supinated.
2. One end of the strap 54 is applied by attaching the hook fastener (64 or 66) to the medial side of the ulna, approximately two inches superior to the distal end of the ulna.
3. The strap 54 will travel from the attached point laterally at an angle to allow the strap to lie flat and diagonally across the anterior area of the elbow (and the lateral side of the humerus) to the medial side of the humerus with the arm bent 90 degrees.

4. The strap 54 is attached with the hook fastener 68 to the posterior side of the humerus at a point that is superior to the belly of the triceps.
5. The strap 54 is then applied to the anterior portion of the elbow, over the top of the first part of the strap (from step 3), crossing the elbow to the lateral side of the forearm. The strap lies flat across the anterior portion of the elbow.
6. The strap 54 travels to the lateral side of the radius (forearm) and the opposite hook fastener (64, 66) is attached to the sleeve 52 approximately two inches superior to the distal head of the radius.
7. The tension of the strap 54 and the initial amount of elbow flexion, can be adjusted to limit the extension of the arm and pronation of the hand up to the point of pain when the arm is extended while the brace 50 is applied to the arm 10.

The final end of the strap applies force which pulls the hand in a pronation direction.

Figure 8:
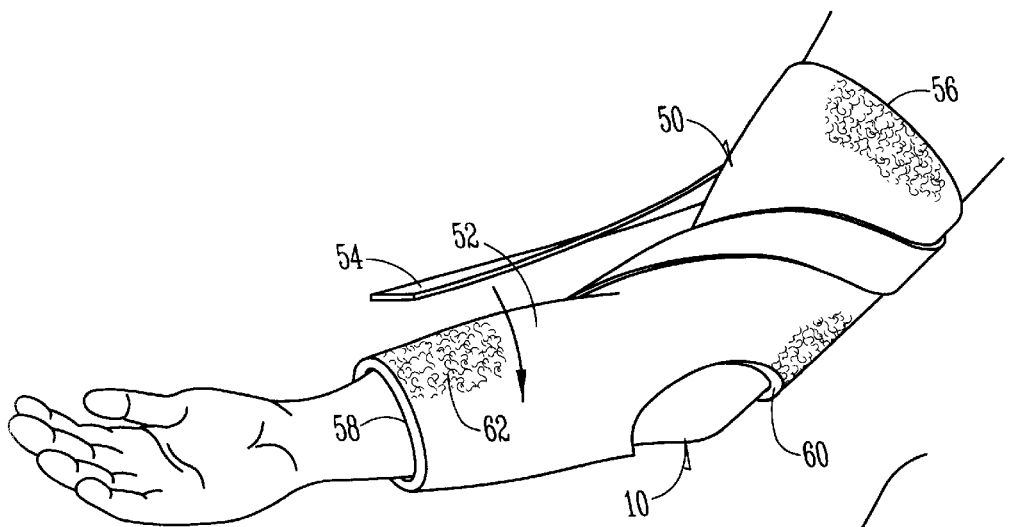
FIG. 8 illustrates the application of the brace shown in FIG. 6.

FIGS. 6 and 8 illustrate the brace 50 applied using an alternate method. The alternate method is used to assist in preventing and treating both elbow hyper-extension and hand hyper-supination. Again, the sleeve is first placed on the arm 10 with the mid sleeve opening 60 positioned on the posterior side of the elbow. The olecranon process is centered in the opening 60. The strap 50 is then applied to the right arm of the wearer using the following steps:

1. The elbow is flexed 90° with the hand supinated.
2. One end of the strap 54 is applied by attaching the hook fastener (64 or 66) to the lateral side of the radius, approximately two inches superior to the distal end of the radius.
3. The strap 54 will travel from the attached point medially at an angle to allow the strap to lie flat and diagonally across the anterior area of the elbow (and the medial side of the humerus) to the lateral side of the humerus with the arm bent 90 degrees.
4. The strap 54 is attached with the hook fastener 68 to the posterior side of the humerus at a point that is superior to the belly of the triceps.
5. The strap 54 is then applied to the anterior portion of the elbow, over the top of the first part of the strap (from step 3), crossing the elbow to the medial side of the forearm. The strap lies flat across the anterior portion of the elbow.
6. The strap 54 travels to the medial side of the forearm and the opposite hook fastener (64, 66) is attached to the sleeve 52 approximately two inches superior to the distal head of the ulna.
7. The tension of the strap 54 and the initial amount of elbow flexion, can be adjusted to limit the extension of the arm and supination of the hand up to the point of pain when the arm is extended while the brace 50 is applied to the arm 10.

The final end of the strap 54 applies force which pulls the hand in a supination direction.

When selecting the method of applying the strap 54, the user must identify what part of the elbow is hurting or what part needs to be protected. For example, if the user has pain along the lateral side of the radius and in the belly of the Brachialis 22, the first method (FIGS. 9 and 10) should be used.

The crossing of the strap 54 on the anterior portion of the elbow is in the position to stabilize the elbow joint. This stabilization is accomplished by reinforcing the position and tightness of the ligaments joining the medial and lateral condyles of the humerus and the superior heads of both the radius and the ulna (see FIG. 1). The stabilization of a joint improves the amount of control individuals have on their movements. As a result of this improved control, accuracy and confidence are noticeably increased. The brace 50 is used not only to control the amount of extension of the elbow, but also the rotation of the hand either in the supination or pronation of the hand.

One adjustment that can be made to the above methods is to pronate the wrist so that the end of the strap can be applied further down on the lateral side of the sleeve 52. Or, the amount of tension in the strap can be adjusted. An increase of the amount of tension on the strap will enhance the hyper-supination protection. Alternately, the wrist can be supinated so that the end of the strap can be applied further down on the lateral side of the sleeve 52.

The brace 50 and method of applying the brace 50 functions like the anatomy of the arm without causing stresses that produce unintended (and damaging) consequences.

The preferred embodiment of the present invention has been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. A method of providing stability for an elbow comprising the steps of:
   providing an elastic sleeve having opposite medial and lateral sides and a posterior portion;
   providing an elastic strap, the elastic strap having a first end, a second end, and a center portion, said first end, second end and center portion each having a fastener thereon;
   identifying the part of the elbow that needs to be protected as a result of an injury or as a preventive measure;
   applying the sleeve to the elbow of a user;
   angularly flexing the elbow with the hand in a supinated or pronated position;
   applying the elastic strap to the elastic sleeve by attaching the first end's fastener to a first side of the sleeve and wrapping the strap laterally at an angle to allow the strap to lie flat and diagonally across the anterior area of the elbow around to and attaching the center portion's fastener to the posterior portion of the sleeve at a point that is superior to the belly of the triceps, then wrapping the strap in a figure eight configuration and attaching the second end's fastener to the opposite side of the sleeve, wherein either the medial or lateral side of the sleeve is selected as the first side depending on the identified part of the elbow that needs to be protected.

2. The method of claim 1 wherein the elastic strap is provided separate from the elastic sleeve.

3. The method of claim 1 further comprising the steps of placing the elastic sleeve around the arm of a user before applying the elastic strap, and applying the elastic strap while the hand of the user is in a supinated position.

4. The method of claim 3 wherein the strap is applied while the elbow is flexed approximately 90 degrees.

5. The method of claim 1 wherein the first end of the strap is applied to the medial side of the elastic sleeve.

6. The method of claim 5 wherein the first end of the strap is attached to the medial side of the sleeve approximately two inches superior to the distal end of the ulna of the user's arm.

7. The method of claim 6 wherein the second end of the strap is attached to the lateral side of the elastic sleeve.

8. The method of claim 7 wherein the second end of the strap is attached to the lateral side of the sleeve approximately two inches superior to the distal end of the radius of the user.

9. The method of claim 5 wherein the strap pulls the hand of a user in a supinated direction.

10. The method of claim 1 wherein the first end of the strap is applied to the lateral side of the elastic sleeve.

11. The method of claim 6 wherein the second end of the strap is attached to the medial side of the elastic sleeve.

12. The method of claim 1 further comprising the step of adjusting the tension of the elastic strap and the initial amount of elbow flexion to limit the extension of the arm and the supination of the hand a desired amount.

13. A method of supporting an elbow joint of a user comprising the steps of:

providing an elastic sleeve having a medial, lateral, and a back side;

providing an elastic strap, the elastic strap having first and second ends and a middle portion;

placing the elastic sleeve over the arm of the user in the proximity of the elbow of the user with the elbow in a bent position;

securing the first end of the strap to the medial side of the sleeve in the proximity of the forearm of the user;

wrapping the strap over the anterior portion of the elbow, around the posterior side of the humerus of the arm, attaching the middle portion of the strap to the sleeve at a point that is superior to the belly of the triceps, back over the anterior portion of the elbow, and to the lateral side of the sleeve; and securing the second end of the strap to the lateral side of the sleeve in the proximity of the forearm of the user.

14. The method of claim 1 where in the angular flexing is at 90°.

* * * * *